US012746399B2

(12) United States Patent
Shahandeh et al.

(10) Patent No.: US 12,746,399 B2
(45) Date of Patent: Sep. 29, 2026

(54) METHOD AND IMPLANTABLE SYSTEM FOR CONSTANT CURRENT PACING

(71) Applicant: Pacesetter, Inc., Sylmar, CA (US)

(72) Inventors: Reza Shahandeh, Tarzana, CA (US); Ninous Davoudi, San Jose, CA (US); Frank Lee, San Leandro, CA (US); David Doudna, Sunnyvale, CA (US); Jeffery Crook, Belmont, CA (US)

(73) Assignee: Pacesetter, Inc., Sylmar (CA)

( * ) Notice: Subject to any disclaimer, the term of this patent is extended or adjusted under 35 U.S.C. 154(b) by 0 days.

(21) Appl. No.: 18/595,619

(22) Filed: Mar. 5, 2024

(65) Prior Publication Data

US 2025/0281764 A1 Sep. 11, 2025

Related U.S. Application Data

(63) Continuation of application No. 17/357,966, filed on Jun. 24, 2021, now Pat. No. 11,957,919.

(51) Int. Cl.
*A61N 1/39* (2006.01)
*A61N 1/05* (2006.01)
(Continued)

(52) U.S. Cl.
CPC ......... *A61N 1/3752* (2013.01); *A61N 1/0563* (2013.01); *A61N 1/365* (2013.01); *A61N 1/36585* (2013.01); *A61N 1/36592* (2013.01); *A61N 1/3706* (2013.01); *A61N 1/37512* (2017.08); *A61N 1/378* (2013.01);
(Continued)

(58) Field of Classification Search
CPC ........... A61N 1/39622; A61N 1/36585; A61N 1/36592; A61N 1/3706; A61N 1/378; A61N 1/0504; H03K 3/017
See application file for complete search history.

(56) References Cited

U.S. PATENT DOCUMENTS 5,312,455 A 5/1994 Zadeh
5,782,883 A * 7/1998 Kroll .................... A61N 1/3918 607/14
(Continued)

FOREIGN PATENT DOCUMENTS

WO WO-2011146498 A2 * 11/2011 ............... H03K 3/57

OTHER PUBLICATIONS

First Office Action mailed Jun. 10, 2026 for corresponding Chinese Patent Application No. 202210698905.5. English translation is provided.

*Primary Examiner* — Carl H Layno
*Assistant Examiner* — Aya Ziad Bakkar
(74) *Attorney, Agent, or Firm* — Dean D. Small; Carroll, Hoette & Butscher, LLC

(57) ABSTRACT

An implantable system includes an implantable medical device (IMD) and a non-transvenous lead that is configured to be implanted outside of a heart. The IMD includes an output configured to be connected at least to the lead, a current generator (CG) circuit configured to generate pacing pulses, a switching circuit coupled between the CG circuit and the output, one or more capacitors coupled in parallel with the CG circuit and the switching circuit, and a control circuit coupled to the CG circuit. The control circuit is configured to manage the CG circuit to generate the pacing pulses with a constant current at the output.

17 Claims, 6 Drawing Sheets

(51) Int. Cl.

| | |
|---|---|
| ***A61N 1/365*** | (2006.01) |
| ***A61N 1/37*** | (2006.01) |
| ***A61N 1/375*** | (2006.01) |
| ***A61N 1/378*** | (2006.01) |
| ***H03K 3/017*** | (2006.01) |

(52) U.S. Cl.
CPC ......... *A61N 1/39622* (2017.08); *H03K 3/017* (2013.01); *A61N 1/0504* (2013.01)

(56) References Cited

U.S. PATENT DOCUMENTS

| | | | | |
|---|---|---|---|---|
| 7,016,738 | B1 | 3/2006 | Karunasiri | |
| 10,675,471 | B2 | 6/2020 | Zhang et al. | |
| 2003/0088282 | A1 | 5/2003 | Ostroff | |
| 2010/0324618 | A1 | 12/2010 | Wanasek | |
| 2019/0329041 | A1* | 10/2019 | Corndorf ........... | A61N 1/36125 |

* cited by examiner

METHOD AND IMPLANTABLE SYSTEM FOR CONSTANT CURRENT PACING

CROSS-REFERENCE TO RELATED APPLICATIONS

This application is a continuation of U.S. Non-Provisional application Ser. No. 17/357,966, filed Jun. 24, 2021, now U.S. Pat. No. 11,957,919, which is hereby incorporated by reference in its entirety.

FIELD

Embodiments of the present disclosure generally relate to methods and implantable systems for delivering electrical stimulation therapy to a patient heart, and more specifically to delivering constant current pacing pulses to treat arrhythmia.

BACKGROUND

Implantable medical devices (IMDs) include electrodes disposed on electrical leads and/or a housing of the IMD, and the electrodes deliver electrical stimulation therapy to the heart of a patient. The electrical stimulation therapy can include different types of stimulation, including pacing pulses and shocks. The shocks are used for cardioversion and/or defibrillation, and are higher energy (e.g., higher voltages) than the pacing pulses. The IMD may deliver the electrical stimulation therapy based on sensed cardiac electrical signals that indicate an arrhythmia, or abnormal heart rhythm. The IMD may select the type of stimulation to be administered based on determined properties of the arrhythmia, such as whether the arrhythmia is bradycardia, tachycardia, or fibrillation. For example, upon detecting bradycardia, the IMD may provide pacing pulses to the heart. In another example, the IMD may provide cardioversion and/or defibrillation shocks in response to detecting fibrillation. Due to the difference in energy output, the IMD may include one circuit designed for generating the pacing pulses and a different, higher voltage circuit for generating the shocks.

One example IMD that can provide the pacing pulses and shocks is an implantable cardioverter defibrillator (ICD). Some ICDs utilize leads that are non-transvenous and extracardiovascular, such that the leads are not threaded through the veins and are outside of the cardiovascular system of the patient. The leads may be disposed on or proximate to the sternum or ribcage. Because the electrodes on the leads are not in intimate contact with the cardiac tissue, the ICDs have to increase the voltages of the electrical stimulation therapies delivered to the heart in order to effectively capture the heart, relative to leads with electrodes that are located in the heart or closer to the heart.

A need remains for methods and implantable devices that can efficiently and effectively deliver multiple phases of electrical stimulation therapy, including both cardioversion and/or defibrillation shocks and pacing pulses, with fewer and/or smaller components to reduce costs and patient discomfort.

SUMMARY

In accordance with an embodiment, an implantable system is provided that includes a non-transvenous lead configured to be implanted outside of a heart and an implantable medical device (IMD). The IMD includes an output configured to be connected at least to the lead, a current generator (CG) circuit configured to generate pacing pulses, a switching circuit coupled between the CG circuit and the output, one or more capacitors coupled in parallel with the CG circuit and the switching circuit, and a control circuit coupled to the CG circuit. The control circuit is configured to manage the CG circuit to generate the pacing pulses with a constant current at the output.

Optionally, the CG circuit is configured to generate the pacing pulses, and the output is configured to receive the pacing pulses, independent of the one or more capacitors and while the one or more capacitors are electrically connected in parallel with the CG circuit and switching circuit. Optionally, the pacing pulses are not generated by the one or more capacitors.

Optionally, the control circuit is configured to manage generation of the pacing pulses during at least one of post-shock pacing, anti-tachycardia pacing, or burst fibrillation. Optionally, the control circuit is configured to vary a duty cycle of control signals supplied to the CG circuit to define a shape of the pacing pulses that have the constant current. Optionally, wherein the control circuit is configured to vary a duty cycle of control signals supplied to the CG circuit to define a pulse width of the pacing pulses that have the constant current.

Optionally, the system also includes one or more processors that, when executing program instructions, are configured to detect an arrhythmia based on signals indicative of heart activity; and manage delivery of a multi-phase therapy that includes first and second phase therapies. During the first phase therapy, one or more shocks are powered from the one or more capacitors. During the second phase therapy, the pacing pulses are delivered by the CG circuit while the one or more capacitors are electrically connected in parallel with the CG circuit and the switching circuit.

Optionally, the CG circuit includes a transformer, and the control circuit is configured to control the CG circuit to activate a primary winding of the transformer while the switching circuit provides a closed, electrically conductive pathway between a secondary winding of the transformer and the output.

Optionally, the control circuit is further configured to manage the switching circuit to provide a closed, electrically conductive pathway between the CG circuit and the output during the generation of each of the pacing pulses by the CG circuit.

Optionally, the CG circuit includes a flyback transformer, a switch device electrically connected to a primary winding of the flyback transformer, and an output diode electrically connected to a secondary winding of the flyback transformer.

In one or more embodiments, a computer-implemented method for delivering stimulation therapy is provided. The method includes managing, via a control circuit, a current generator (CG) circuit of an implantable medical device (IMD) to generate pacing pulses with a constant current at an output of the IMD. The output is configured to be connected at least to a non-transvenous lead configured to be implanted outside of a heart. The IMD further includes a switching circuit coupled between the CG circuit and the output, and one or more capacitors coupled in parallel with the CG circuit and the switching circuit.

Optionally, the method also includes detecting, via one or more processors, an arrhythmia based on signals indicative of heart activity. Responsive to detecting the arrhythmia, the method includes delivering the pacing pulses generated by the CG circuit via the non-transvenous lead, while the one or more capacitors are electrically connected in parallel with the CG circuit and the switching circuit.

Optionally, the managing of the CG circuit to generate the pacing pulses with the constant current is a second phase therapy of a multi-phase therapy. The method further includes managing, via the control circuit, the one or more capacitors to power one or more shocks during a first phase therapy of the multi-phase therapy.

Optionally, the managing of the CG circuit includes controlling the CG circuit to generate the pacing pulses, for receipt of the pacing pulses at the output, independent of the one or more capacitors and while the one or more capacitors are electrically connected in parallel with the CG circuit and switching circuit. Optionally, the managing of the CG circuit includes controlling the CG circuit to generate the pacing pulses without the one or more capacitors generating the pacing pulses.

Optionally, the managing of the CG circuit includes controlling the CG circuit to generate the pacing pulses during at least one of post-shock pacing, anti-tachycardia pacing, or burst fibrillation. Optionally, the method includes varying a duty cycle of control signals supplied to the CG circuit to define at least one of a shape or a pulse width of the pacing pulses that have the constant current.

Optionally, the method includes managing the switching circuit, via the control circuit, to provide a closed, electrically conductive pathway between the CG circuit and the output during the generation of each of the pacing pulses by the CG circuit.

Optionally, the CG circuit includes a flyback transformer, a switch device electrically connected to a primary winding of the flyback transformer, and an output diode electrically connected to a secondary winding of the flyback transformer. The managing of the CG circuit includes opening and closing the switch device according to a duty cycle to generate the pacing pulses with the constant current at the secondary winding.

In one or more embodiments, an implantable system is provided that includes a non-transvenous lead configured to be implanted outside of a heart and an IMD. The IMD includes an output configured to be connected at least to the lead, a current generator (CG) circuit comprising a flyback transformer configured to generate pacing pulses, a switching circuit coupled between the CG circuit and the output, one or more capacitors coupled in parallel with the CG circuit and the switching circuit, and a control circuit coupled to the CG circuit. The control circuit is configured to detect an arrhythmia based on signals indicative of heart activity, and manage delivery of a multi-phase therapy that includes first and second phase therapies responsive to detection of the arrhythmia. During the first phase therapy, one or more shocks at the output are powered from the one or more capacitors. During the second phase therapy, the pacing pulses are generated by the CG circuit with a constant current at the output, while the one or more capacitors are electrically connected in parallel with the CG circuit and the switching circuit.

Optionally, during the second phase therapy, the switching circuit is configured to provide a closed, electrically conductive pathway between the CG circuit and the output during the generation of each of the pacing pulses by the CG circuit, such that each pacing pulse of the pacing pulses is directly conveyed from a secondary winding of the flyback transformer through the switching circuit to the output, while the one or more capacitors are electrically connected in parallel with the CG circuit and the switching circuit.

DETAILED DESCRIPTION

Figure 1:
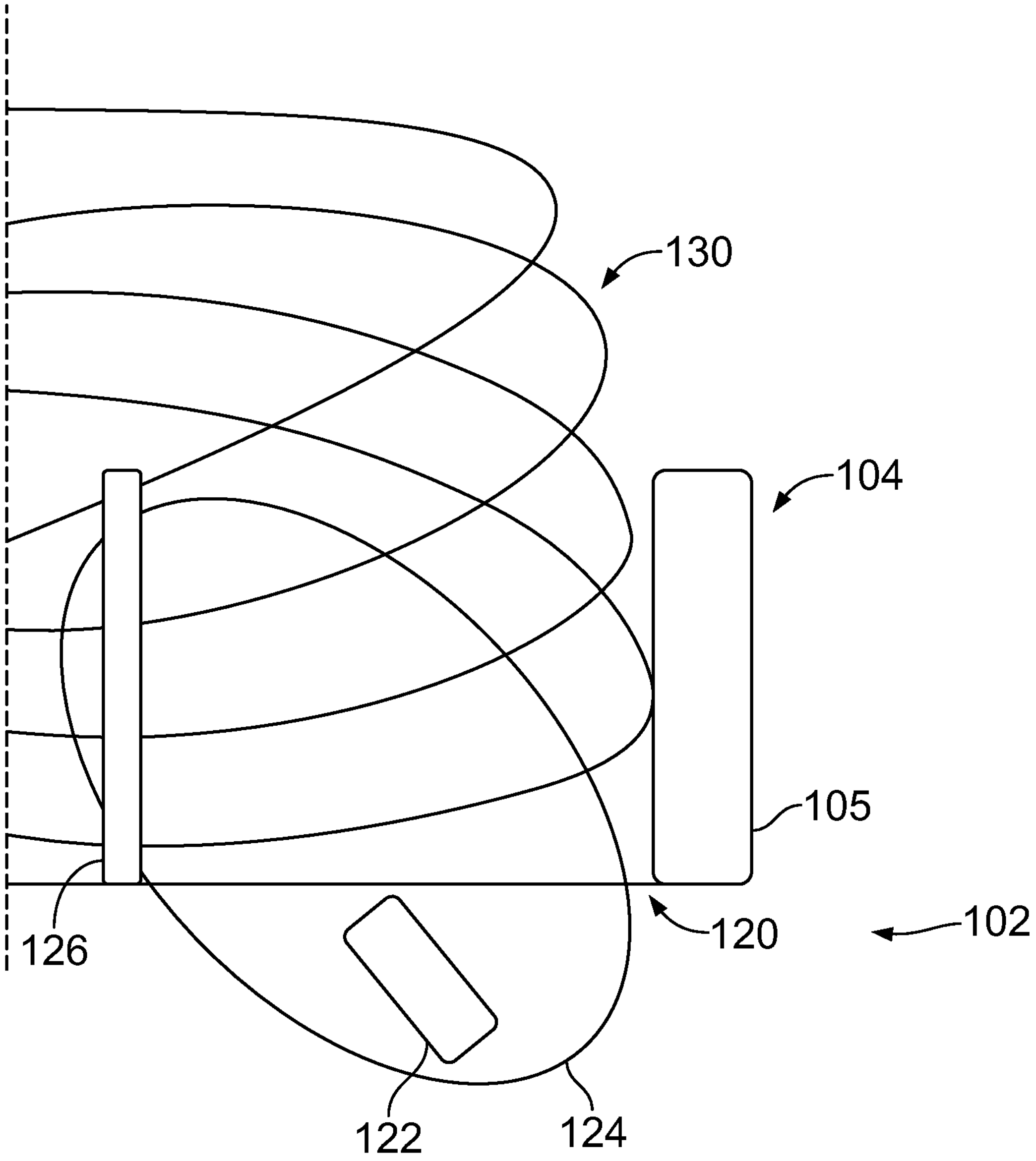
FIG. 1 illustrates a graphical representation of an implantable system that is configured to apply electrical stimulation cardiac therapy in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to “one embodiment” or “an embodiment” (or the like) means that a particular feature, structure, or characteristic described in connection with the embodiment is included in at least one embodiment. Thus, appearances of the phrases “in one embodiment” or “in an embodiment” or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

According to at least one embodiment, an implantable system is provided to deliver pacing pulses with a constant current to the patient in which the system is implanted. The implantable system includes circuitry that has dual-use functionality. For example, the same circuitry can be used to deliver shocks for cardioversion and/or defibrillation (CV/DF) and to deliver lower-energy pacing pulses for other types of therapy such as post-shock therapy, anti-tachycardia pacing (ATP), and/or burst fibrillation during the implant procedure. Known IMDs with the capability to provide both shock therapy and pacing therapy have two discrete circuits, including a high voltage circuit for shocks and a low voltage circuit for the pacing. By providing a single circuit with dual functionality for both shocks and pacing pulses, the implantable system described herein can reduce the number of parts (e.g., circuit hardware) within the IMD, which can reduce manufacturing costs and may also enable reducing the size of the IMD to beneficially occupy less space within the patient.

The term "constant current" as used herein shall mean that each pacing pulse has a generally fixed or common output current. The output current is fixed such that the intensity is generally uniform throughout the pulse width, between the leading and trailing edges of the pulse of energy. The current is generally fixed and uniform, meaning that slight fluctuations, or ripples, in the current waveform may be present, although the intensity throughout the pulse width remains within a designated threshold margin of the output current value, such as +/−10%, 5%, or the like.

The term "post-shock pacing" shall refer to pacing pulses delivered during a time period immediately after delivering shock therapy to the heart via an IMD. In a non-limiting example, the pacing pulses during post-shock pacing may be delivered at about 50-60 pulses per minute (e.g., around 1 pulse per second) for a period that lasts up to 30 seconds after each set of one or more shocks.

The term "burst fibrillation" shall refer to high frequency pacing pulses often used to initiate or induce atrial fibrillation for testing an IMD during implantation and set-up of the IMD. For example, a recently-implanted IMD may be controlled to provide burst fibrillation pulses to induce fibrillation in the patient, which is then corrected or treated via stimulation therapy provided by the IMD. Burst fibrillation pulses can also be used for electrophysiological studies. The term "high frequency" as used in connection with pacing pulses and pacing therapy shall refer to delivering pacing pulses at a rate greater than a rate associated with anti-tachycardia pacing, namely at a rate of at least 30 Hz.

The term "medium-voltage shock" (MV shock) shell refer to defibrillation stimulus delivered at an energy level sufficient to terminate a defibrillation episode in a heart, wherein the energy level is defined in Joules, pulse width, and/or maximum charge voltage. A MV shock from an IMD with a transvenous lead will have a lower maximum energy and/or charge voltage than an MV shock from a subcutaneous IMD with a subcutaneous lead (e.g. non-transvenous, parasternal, extra-cardiovascular, and the like). In connection with an IMD having a subcutaneous lead, the term MV shock refers to defibrillation stimulation that has an energy level that is no more than 30 J, and more preferably between 15 J and 25 J, and/or has a maximum voltage of no more than 500 V, preferably between 100 V and 475 V and more preferably between 400 V and 475 V.

The term "high-voltage shock" (HV shock) shall refer to defibrillation stimulus delivered at an energy level sufficient to terminate a defibrillation episode in a heart. When used in connection with an IMD having a subcutaneous lead, the energy level is defined in Joules to be 30 J or more, and more preferably between 35 J and 45 J. The HV shock is defined in terms of voltage to be 500 V or more, and more preferably between 500 V and 750 V.

The term "subcutaneous" shall mean below the skin, but not intravenous (e.g., non-transvenous). For example, a subcutaneous electrode/lead does not include an electrode/lead located in a chamber of the heart, in a vein on the heart, or in the lateral or posterior branches of the coronary sinus.

The terms "abnormal," or "arrhythmic" are used to refer to events, features, and characteristics of, or appropriate to, an unhealthy or abnormal functioning of the heart. The terms "arrhythmia treatment", "in connection with treating a heart condition" and similar phrases, as used herein include, but are not limited to, delivering an electrical stimulation or drug therapy to a heart condition. By way of example, treating a heart condition may include, in whole or in part, i) identifying a progression of heart failure over time; ii) confirming an arrhythmia identified by an arrhythmia detection process; iii) instructing the patient to perform a posture recalibration procedure; and/or iv) delivering a therapy.

The terms "cardiac activity signals", "cardiac signals", and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes and/or by electrodes positioned within or proximate to the heart wall and/or chambers of the heart.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

FIG. 1 illustrates a graphical representation of an implantable system 102 that is a medical system configured to apply electrical stimulation cardiac therapy in accordance with embodiments herein. The implantable system 102 (also referred to herein as system 102) includes an implantable medical device (IMD) 104 that is configured to provide separate therapies at different energy levels and/or multi-phase therapy. The separate therapies may include one or more shocks delivered at a high or medium voltage, one or more shocks delivered at a high or medium voltage, anti-tachycardia pacing and/or one or more pacing pulses. The multi-phase therapy may include shocks that define a first phase therapy and pacing pulses that define a second phase therapy. The shocks have greater energy (e.g., higher voltage) than the pacing pulses. In an embodiment, the IMD 104 is a subcutaneous IMD (SIMD) implanted in a subcutaneous area exterior to the heart. The SIMD 104 may be positioned in a mid-axillary position along a portion of the rib cage 130 of the patient. The system 102 does not include a transvenous lead.

The IMD 104 includes a case 105 and at least one lead 120 that is connected to the case 105 and extends from the case 105. The "at least one lead" is hereinafter referred to as "the lead," although it should be understood that the term "the lead" may refer to a single lead or to multiple leads. The case 105 holds pulse generation circuitry and a power source for powering the pulse generation circuitry to generate electrical pulses.

The lead 120 includes an electrode segment 126 that is used for providing high-voltage shocks for CV/DF and/or for providing lower voltage pacing pulses for ATP, post-shock pacing, and/or burst fibrillation. The electrode segment 126 includes at least one electrode connected to a lead body of the lead 120. The at least one electrode may include a ring electrode, a tip electrode, and/or a coil electrode. The at least one electrode may be utilized to deliver the electrical stimulation therapy to the patient. For example, a shock and/or pacing pulse generated by the pulse generation circuitry in the case 105 is conveyed along the lead body of the lead 120 to the electrode segment 126, at which the at least one electrode delivers the shock and/or pacing pulse to the surrounding tissue of the patient. Optionally, the lead 120 may include one or more electrodes used for sensing cardiac activity (e.g., electrical cardiac signals). Optionally, an electrode used for sensing may also be used to deliver the electrical stimulation therapy. The case 105 includes a housing that may form or include an electrode, referred to as a "can" electrode, for the delivery of the shocks and/or pacing pulses.

In an embodiment, the lead 120 is a non-transvenous lead that is implanted outside of the heart of the patient. For example, the lead 120 may be an extra-cardiovascular lead that is located outside of the pericardium surrounding the heart and outside of the blood vessels. The electrode segment 126 of the lead 120 may extend extra-thoracically outside of the sternum and ribcage or intra-thoracically inside of the sternum and ribcage (while spaced apart from myocardial tissue). The electrode segment 126 may be positioned parasternally within one to three centimeters from the sternum. In the illustrated embodiment, the lead body extends from the mix-axillary position of the electrode segment 126 along an inter-costal area between ribs to the case 105 of the IMD 104. The electrode segment 126 may include at least one coil electrode for providing high voltage CV/DF shocks. A coil electrode may be located proximate to the xiphoid process.

In an alternative embodiment, the lead 120 may include multiple electrode segments spaced apart from one another with an electrical gap therebetween. One electrode segment may be positioned along an anterior of the chest, while another electrode segment may be positioned along a lateral and/or posterior region of the patient. The electrode segments may be portions of the same lead 120, or the electrode segments may be portions of different leads. When portions of the same lead, the lead body of the lead extends across the gap. The electrode segments may be positioned subcutaneously at a level that aligns with the heart of the patient for providing a sufficient amount of energy to capture the heart for defibrillation.

The system 102 optionally also includes a leadless pacemaker 122 implanted within the heart, such as at an apex 124 of the right ventricle. The pacemaker 122 may provide a different type or phase of therapy than the multi-phase therapy provided by the IMD 104. For example, the pacemaker 122 may deliver pacing pulses that define a third phase therapy. The pacing pulses provided by the pacemaker 122 may be more regularly delivered over a period of time (e.g., hour, day, etc.) and lower voltage than the pacing pulses provided by the IMD 104. The pacemaker 122 may deliver chronic pacing therapy, and the IMD 104 may deliver intermittent shock therapy and/or pacing therapy based on sensed cardiac activity.

Figure 2:
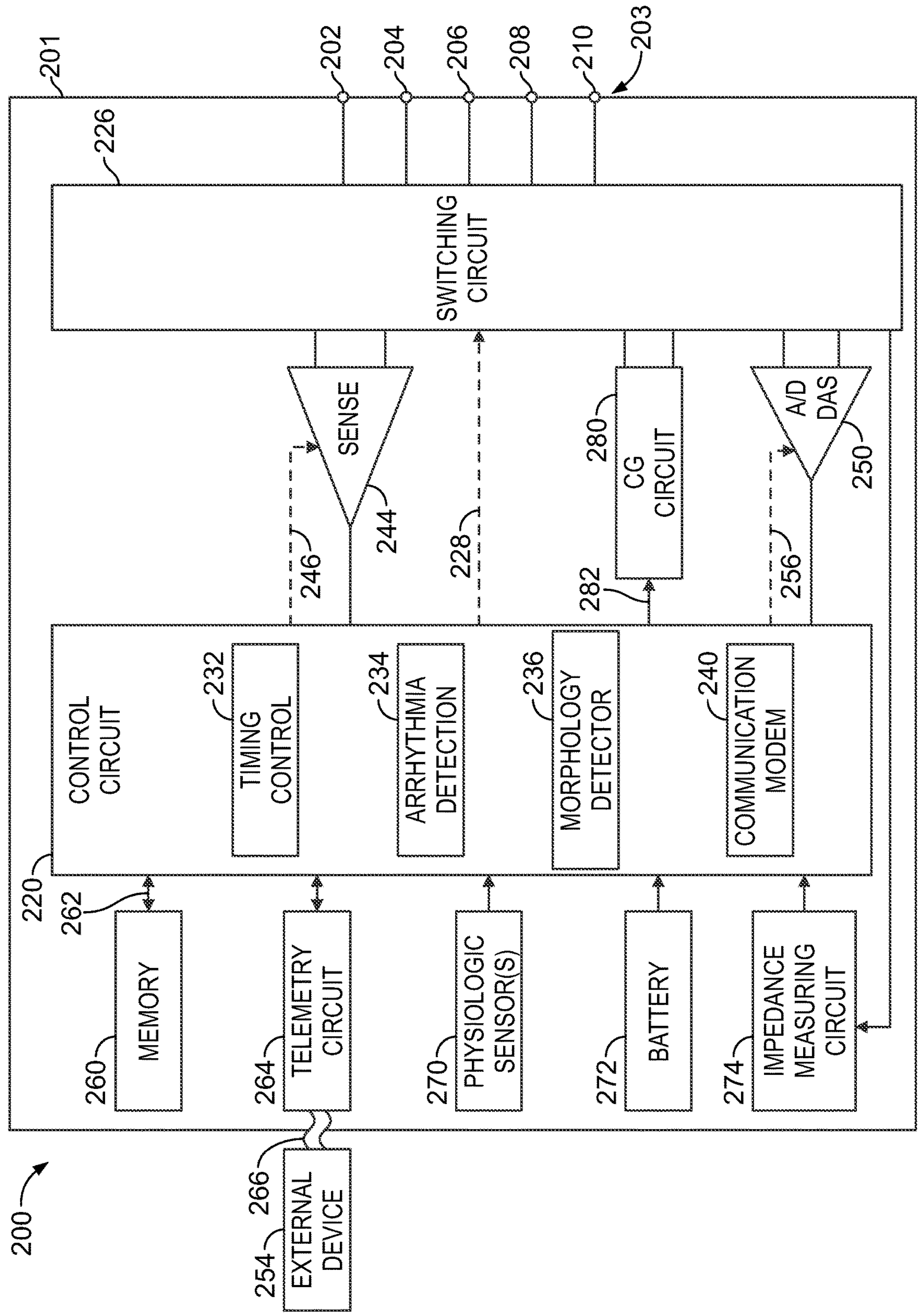
FIG. 2 shows a block diagram of an exemplary implantable medical device (IMD) that is configured to be implanted into the patient.

FIG. 2 shows a block diagram of an exemplary IMD 200 that is configured to be implanted into the patient. The IMD 200 may treat both fast and slow arrhythmias with stimulation therapy, including CV/DF shock stimulation and pacing stimulation. The IMD 200 may represent the IMD 104 of the implantable system 102 shown in FIG. 1.

The IMD 200 has a case 201 (or housing) to hold electronic/computing components. The case 201 may be the case 105 shown in FIG. 1. The case 201 may be programmably selected to act as the return electrode for certain stimulus modes (e.g., phases of therapy). The case 201 further includes an output 203 or connector with a plurality of terminals 202, 204, 206, 208, 210. The terminals 202, 204, 206, 208, 210 may be connected to leads that extend to various locations within the patient around the heart. The leads have electrodes that may include various combinations of ring electrodes, tip electrodes, coil electrodes, and the like.

The IMD 200 includes a control circuit 220 that controls various operations of the IMD 200, including. cardiac monitoring and stimulation therapy. The control circuit 220 may be a microcontroller that includes a microprocessor (or equivalent control circuitry), one or more processors, RAM and/or ROM memory, logic and timing circuitry, state machine circuitry, and/or input/output (I/O) circuitry.

The IMD 200 includes a switching circuit 226 to enable different electrode configurations (e.g., vectors) for delivering stimulation therapy under the control of the control circuit 220. The switching circuit 226 may include multiple switches for connecting the desired terminals 202, 204, 206, 208, 210 at the output 203 to the electrodes of the leads, thereby facilitating electrode programmability. The switching circuit 226 is controlled by control signals 228 generated by the control circuit 220.

The IMD 200 further includes a current generator (CG) circuit 280 that generates stimulation pulses for controlling and/or modifying the rhythm of the heart. The CG circuit 280 is configured to provide separate therapies at different energy levels and/or multi-phase therapy. The separate therapies may include one or more shocks delivered at a high or medium voltage, one or more shocks delivered at a high or medium voltage, anti-tachycardia pacing and/or one or more pacing pulses. Additionally or alternatively, the CG circuit 280 is configured to provide multi-phase therapy, as described herein. The CG circuit 280 is controlled by the control circuit 220 via control signals 282. The CG circuit 280 can generate stimulation pulses of low (e.g., up to 5 joules), moderate or medium (e.g., 5-30 joules), and/or high energy (e.g., at least 30 joules) for the subcutaneous lead, as controlled by the control circuit 220. The stimulation pulses are conveyed by the switching circuit 226 to a selected set of the terminals 202, 204, 206, 208, 210 to deliver the stimulation pulses via a desired configuration of electrodes.

The IMD 200 includes a sensing circuit 244 selectively coupled to one or more electrodes that perform sensing operations through the switching circuit 226 to detect cardiac activity. The sensing circuit 244 may include dedicated sense amplifiers, multiplexed amplifiers, or shared amplifiers. The sensing circuit 244 may operate in a unipolar sensing configuration or a bipolar sensing configuration. The output of the sensing circuit 244 is connected to the control circuit 220. In response to the cardiac activity sensed by the sensing circuit 244, the control circuit 220 may trigger or inhibit the electrical stimulation circuit 280. The sensing circuit 244 receives a control signal 246 from the control circuit 220 for purposes of controlling the gain, threshold, polarization, and timing of any blocking circuitry (not shown) coupled to the sensing circuit 244. Optionally, the IMD 200 may include multiple sensing circuits 244.

The IMD 200 further includes an analog-to-digital (A/D) data acquisition system (DAS) 250 coupled to terminals 202, 204, 206, 208, 210 via the switching circuit 226 to sample cardiac signals across any pair of desired electrodes. The A/D DAS 250 is configured to acquire intracardiac electrogram signals, convert the raw analog data into digital data and store the digital data for later processing and/or telemetric transmission to an external device 254 (e.g., a programmer, local transceiver, or a diagnostic system analyzer). The A/D DAS 250 is controlled by a control signal 256 from the control circuit 220.

The control circuit 220 is operably coupled to a memory 260 by a suitable data/address bus 262. The memory 260 may store programmed operating instructions and/or parameters used by the control circuit 220 to operate the IMD 200. The memory 260 may also store data associated with the detection and determination of arrhythmias.

The IMD 200 is communicatively connected to an external device 254. The external device 254 may communicate with a telemetry circuit 264 of the IMD 200 through a communication link 266. The external device 254 facilitates access by a physician to patient data as well as permits the physician to review real-time cardiac signals while collected by the IMD 200.

The IMD 200 may also include one or more physiological sensors 270 that are used to adjust pacing stimulation rates, detect changes in cardiac output, changes in the physiological condition of the heart, and/or diurnal changes in activity (e.g., detecting sleep and wake states). Examples of physiological sensors 270 might include sensors that, for example, sense respiration rate, pH of blood, ventricular gradient, activity, body movement, position/posture, minute ventilation (MV), and/or the like. While shown as being included within the IMD 200, the physiological sensor(s) 270 may be external to the IMD 200, yet still implanted within the patient or carried by the patient.

A battery 272 of the IMD 200 provides operating power to all of the components in the IMD 200. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 200 further includes an impedance measuring circuit 274, which can be used for many things, including sensing respiration phase. The IMD 200 is further equipped with a communication modem (modulator/demodulator) 240 to enable wireless communication with the external device 254 and/or other external devices.

The control circuit 220 may further include other dedicated circuitry and/or firmware/software components that assist in monitoring various conditions of the patient's heart and managing stimulation therapies. For example, the control circuit 220 may include a timing control (module) 232, an arrhythmia detector (module) 234, and a morphology detector (module) 236. The timing control 232 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The morphology detector 236 is configured to review and analyze one or more features of the morphology of CA signals. For example, the morphology detector 236 may analyze the morphology of detected R waves to determine whether to include or exclude one or more heart beats from further analysis. For example, the morphology detector 236 may be utilized to identify non-conducted ventricular events, such as premature ventricular contractions, ventricular tachycardia, and the like.

The arrhythmia detector 234 is configured to apply one or more arrhythmia detection algorithms for detecting arrhythmia conditions. The arrhythmia detector 234 may analyze CA signals to identify potential atrial fibrillation (AF) episodes as well as other arrhythmias (e.g., tachycardias, bradycardias, asystole, etc.). In a non-limiting example, the arrhythmia detector 234 may apply the AF detection algorithm described in U.S. Pat. No. 8,121,675, entitled, "Device and method for detecting atrial fibrillation," the complete subject matter of which is incorporated herein by reference.

The arrhythmia detector 234 and morphology detector 236 operate in combination. The control circuit 220 collects CA signals for a collection window for a predetermined period of time or number of beats (e.g., one minute or 68 beats). The arrhythmia detector 234 detects R waves within the CA signals for the collection window. Optionally, the morphology detector 236 may analyze the morphology of the R waves in search of non-conducted ventricular events (PVCs or VTs). For example, the morphology detector 236 may compare a morphology of consecutive beats to one or more templates associated with normal/healthy R waves morphologies, PVC morphologies, VT morphologies, and the like. The morphology detector 236 may modify the CA signals by excluding beats that are declared to represent the non-conducted ventricular events (PVCs or VT) to form non-conduction corrected CA signals to improve the specificity of the AF detection. Additionally or alternatively, the morphology detector 236 may determine to block or exclude the entire CA signal in the event that more than a predetermined number of the beats are declared as non-conductive ventricular events.

Figure 3:
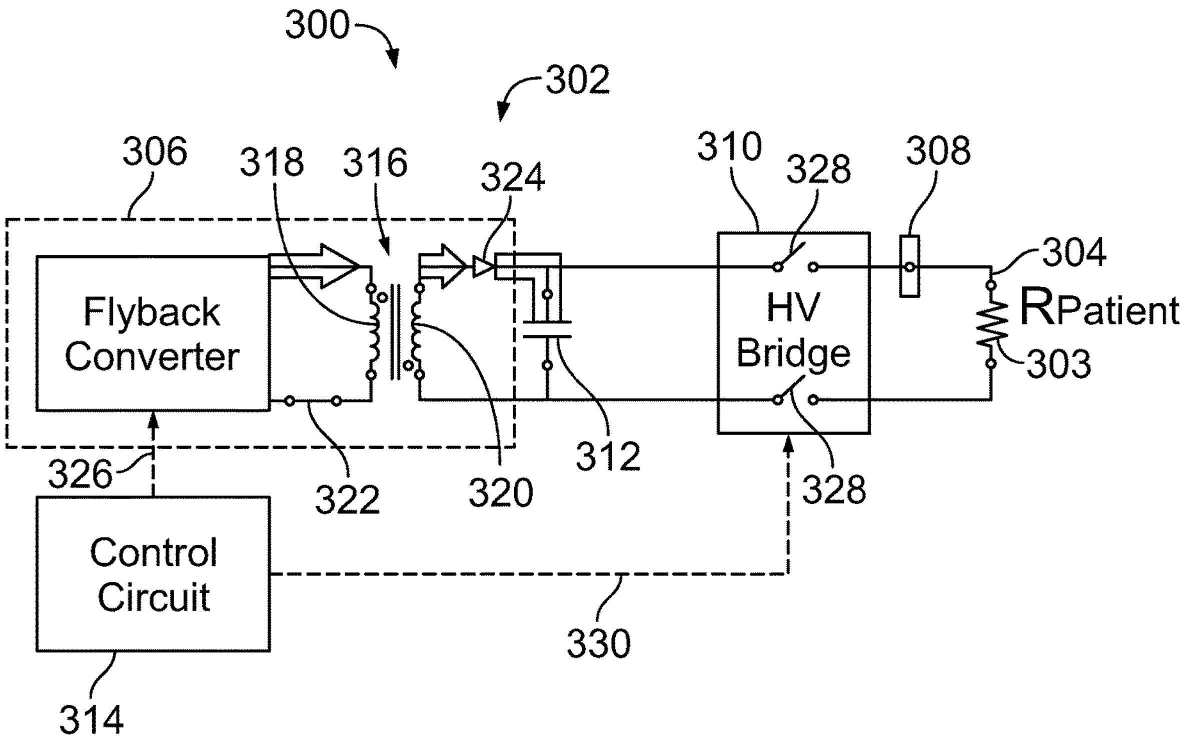
FIG. 3 illustrates a circuit diagram of an implantable system according to an embodiment.

FIG. 3 illustrates a circuit diagram of an implantable system 300 according to an embodiment. The implantable system 300 may represent the implantable system 100 shown in FIG. 1. The implantable system 300 includes an IMD 302 operatively coupled to at least one non-transvenous lead 304. The lead 304 may represent the lead 120 in FIG. 1. The lead 304 according to an embodiment is implanted to position one or more electrodes thereof at extra-cardiovascular locations for sensing and/or delivering stimulation therapy. The extra-cardiovascular electrodes of the lead 304 avoid the difficulties associated with threading the lead through veins of the patient into cardiac tissue. The implantable system 300 generates and delivers electrical stimulation therapy to a patient heart, which represents a patient load. The resistive element 303 in FIG. 3 represents the patient load. The patient load may have a resistance around 50 Ohms.

The IMD 302 includes a current generator (CG) circuit 306 configured to generate electrical stimulation pulses. The IMD 302 also includes an output 308 that connects to the lead 304. The output 308 may be a connector, such as a feedthrough assembly. The IMD 302 includes a switching circuit 310 coupled between the CG circuit 306 and the output 308. The IMD 302 further includes one or more capacitors 312 and a control circuit 314. The control circuit 314 is operatively (e.g., communicatively) connected to the CG circuit 306, and manages the CG circuit to generate stimulation pulses at different electrical properties (e.g., voltages, currents, pulse widths, polarities, etc.). The IMD 302 may represent the IMD 104 shown in FIG. 1 and/or the IMD 200 shown in FIG. 2. For example, the output 308 may represent the output 203; the CG circuit 306 may represent the CG circuit 280; the switching circuit 310 may represent the switching circuit 226; and the control circuit 314 may represent the control circuit 220. Alternatively, the IMD 302 may be similar to, but different than, the IMD 200 in FIG. 2.

The one or more capacitors 312 are coupled in parallel with the CG circuit 306 and the switching circuit 310. One capacitor 312 is shown in FIG. 3. Optionally, the IMD 302 may include a bank of multiple capacitors or other types of electrical energy storage devices at the location of the capacitor 312. In a non-limiting example, the capacitor 312 may have a capacitance of about 100 microfarads with a high voltage rating. The capacitor 312 may be capable of charging to 950 V. The capacitor 312 can be referred to as a high voltage (HV) capacitor.

The CG circuit 306 may include a transformer 316 that includes a primary winding 318 and a secondary winding 320. In an embodiment, the CG circuit 306 includes or defines a flyback converter, and the transformer 316 is a flyback transformer. For example, the transformer 316 is a coupled inductor with a gapped core that can store energy during each cycle prior to discharging the energy to the secondary winding 320. The CG circuit 306 also includes a switch device 322 electrically connected to the primary winding 318. An output diode 324 of the CG circuit 306 is electrically connected to the secondary winding 320. The CG circuit 306 may include additional components, such as one or more capacitors.

The switch device 322 may be an insulated gate bipolar transistor (IGBT), a metal oxide semiconductor field effect transistor (MOSFET), a silicon-controlled rectifier (SCR), or the like. In a preferred embodiment, the switch device 322 is a MOSFET. The switch device 322 is controlled by the control circuit 314 to switch between open and closed states. As used herein, a switch in the open state breaks the circuit to prevent electrical conduction along the circuit pathway, and a switch in the closed state establishes an electrically-conductive circuit pathway to enable electrical conduction along the pathway. For example, when the switch device 322 is in the closed state, the CG circuit 306 receives power (e.g., electrical energy) from a power source, such as the battery 272 in FIG. 2. The CG circuit 306 does not receive power when the switch device 322 is in the open state. The control circuit 314 generates control signals 326 to control the operation of the switch device 322, which establishes the duty cycle of the CG circuit 306.

The switching circuit 310 includes multiple switch devices 328 used to selectively control the delivery of stimulation pulses to the electrodes. The switching circuit 310 represents a high voltage (HV) bridge that is controlled by the control circuit 314, via control signals 330, to selectively electrically connect the CG circuit 306 and the capacitor 312 to the output 308 and the lead 304. Two switch devices 328 are shown in FIG. 3, but the switching circuit 310 may have more than two switch devices 328. The switch devices 328 may be IGBTs, SCRs, MOSFETs, or other switching circuitry. In a preferred embodiment, the switch devices 328 include IGBTs and SCRs. The switching circuit 310 optionally may be arranged in an H-bridge configuration in which two switch devices 328 are coupled in parallel upstream of the output 308 and the patient load 303, and two switch devices 328 are coupled in parallel downstream of the output 308 and patient load 303. Although only a single control signal 330 is illustrated, the switch devices 328 of the switching circuit 310 may be individually controlled by the control circuit 314 to select a therapy delivery vector. For example, the therapy delivery vector may be defined by the particular electrodes of the one or more leads 304 or the case, that are electrically connected via a closed conductive pathway to the capacitor 312. The control circuit 314 achieves the therapy delivery vector by selectively opening (e.g., disabling or turning off to break the conductive pathway) and closing (e.g., enabling or turning on to establish the conductive pathway) each of the switch devices 328.

In an embodiment, the IMD 302 can provide multi-phase therapy using the circuitry illustrated in FIG. 3. The IMD 302 can switch between different phases, or types, of stimulation therapy by controlling the CG circuit 306 and the switching circuit 310, as described herein. A first phase therapy provides one or more shocks for CV/DF. A second phase therapy provides pacing pulses that are lower energy (e.g., voltage) relative to the CV/DF shocks. The pacing pulses in the second phase therapy may be generated to provide post-shock therapy, ATP, burst fibrillation, and/or the like. The IMD 302 operates in a high voltage mode to provide the first phase therapy, and operates in a low voltage mode to provide the second phase therapy. The terms "high voltage" and "low voltage" are used merely for identifying and distinguishing the two operational modes relative to each other.

FIG. 3 illustrates the IMD 302 in the high voltage mode for delivering CV/DF shocks to the patient. The control circuit 314 may enter the high voltage mode in response to detecting an arrhythmia that requires shock therapy, based on signals indicative of heart activity (e.g., CA signals). For example, the detected arrhythmia that triggers the high voltage mode of the IMD 302 may be atrial or ventricular fibrillation or tachycardia. The arrhythmia is detected by one or more processors. In one embodiment, the one or more processors that detect the arrhythmia are components of the control circuit 314, such that the control circuit 314 analyzes the CA signals and makes determinations about the presence or absence of abnormal heart activity. In another embodiment, the one or more processors that detect the arrhythmia are components of another processing device or circuit, either within the same IMD 302 or in a different device. In that case, the control circuit 314 receives a notification signal that the arrhythmia has been detected, and then configures the IMD 302 to provide stimulation therapy in response to the characteristics of the arrhythmia as described in the notification signal.

In the high voltage mode, the control circuit 314 controls the CG circuit 306 and the switching circuit 310 according to a first protocol to deliver the CV/DF shocks. The shocks in the high voltage mode are powered by the capacitor 312. The protocol may include opening the switching circuit 310 to electrically disconnect the output 308 from the capacitor 312 and the CG circuit 306. The control circuit 314 then activates the CG circuit 306 to charge the capacitor 312, while the output 308 remains disconnected. The CG circuit 306 may be activated by cycling the switch device 322 between the open state and the closed state and/or by maintaining the switch device in the closed, conducting state. The CG circuit 306 charges the capacitor 312 by conveying electrical energy from the battery 272 (shown in FIG. 2) or other power source through the CG circuit 306 to the capacitor 312. For example, the electrical energy is inducted across the transformer 316, through the diode 324 to the capacitor 312 (or block of capacitors if more than one capacitor is present). The control circuit 314 may open or deactivate the CG circuit 306 to cease charging the capacitor 312. For example, the control circuit 314 may deactivate the CG circuit 306 maintaining the switch device 322 in the open state.

To deliver the shock pulse, electrical energy stored in the capacitor 312 is directed from the capacitor 312 through the switching circuit 310 to the output 308. This charge transfer may be achieved by selectively closing the appropriate switch devices 328 of the switching circuit 310 to provide an electrically conductive pathway from the capacitor 312 to the output 308 and the one or more electrodes connected thereto. Each shock pulse may be delivered from the capacitor 312 at an energy level sufficient to terminate a fibrillation episode in the heart. The shocks delivered by the non-transvenous (e.g., extra-cardiovascular) lead 304 may have an energy level that is 30 J or more, and more preferably in a range between 35 and 45 J. The shocks delivered by the non-transvenous lead 304 may have a voltage amplitude in a range between 200 V and 750 V, and more preferably a voltage within a range between 500 V and 750 V.

Figure 4:
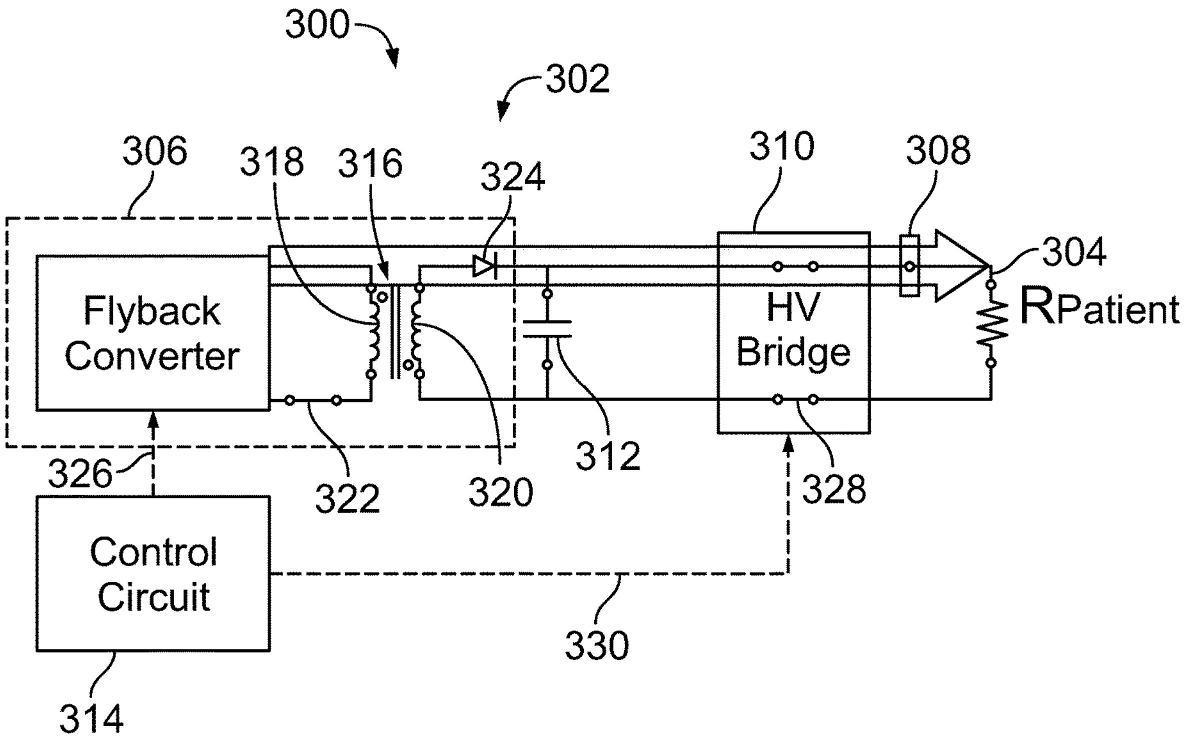
FIG. 4 illustrates the circuit diagram of the implantable system shown in FIG. 3 when an IMD of the implantable system is in a low voltage mode to deliver pacing pulses.

FIG. 4 illustrates the circuit diagram of the implantable system 300 shown in FIG. 3 when the IMD 302 is in the low voltage mode to deliver pacing pulses. In the high voltage mode, the IMD 302 provides the first phase therapy by delivering one or more shocks powered by the capacitor 312. During the second phase therapy of the multi-phase therapy, the IMD 302 delivers pacing pulses using the same circuit components. In an embodiment, the only difference between the high voltage mode to deliver the shock pulses and the low voltage mode to deliver the pacing pulses is the operations of the control circuit 314 to control the CG circuit 306 and the switching circuit 310.

The pacing pulses may be generated in response to a detected arrhythmia that is treated by the pacing pulses. The arrhythmia may be tachycardia, bradycardia, or the like. The IMD 302 may deliver the pacing pulses during post-shock pacing, ATP, burst fibrillation, and/or the like. The post-shock pacing pulses may be delivered during a time period immediately after delivering a shock in the high voltage mode of the IMD 302. For example, the pacing pulses may be delivered at about 50-60 pulses per minute (e.g., around 1 pulse per second) for a period that lasts up to 30 seconds after each shock. The ATP therapy delivers pacing pulses to interrupt a detected tachyarrhythmia, such as ventricular tachycardia (VT). ATP pacing pulses are higher frequency than post-shock pacing pulses. The ATP pacing may provide about six to seven pulses per second. The burst fibrillation pulses are high frequency pacing pulses used to initiate atrial fibrillation for testing IMDs during the implantation and set-up process and/or for electrophysiological studies. For example, after the IMD 302 is implanted, the IMD 302 may be controlled to provide burst fibrillation pacing pulses to induce fibrillation in the patient. The induced fibrillation can be treated via the shock pulses of the IMD 302.

In the low voltage mode, the control circuit 314 manages the CG circuit 306 to generate pacing pulses with a constant current at the output 308. In an embodiment, the current of the pacing pulses may be a value within the range from 50 mA to 500 mA. The pacing pulses generated by the IMD 302 have lower voltages and deliver less energy than the shocks. The pacing pulses delivered via the non-transvenous lead 304 may have voltage amplitudes that are less than 100 V, and more preferably no more than 40 V. The pacing pulses may have an energy level that is no more than 5 Joules, and more preferably less than 1 Joule. The energy of the pacing pulse for a given voltage varies depending on factors such as the pulse width and electrode vector impedance.

In an embodiment, the CG circuit 306, not the capacitor 312, generates the pacing pulses. The pacing pulses in the low voltage mode are not generated by the capacitor 312 (or any other capacitor disposed between the CG circuit 306 and the switching circuit 310). For example, electrical energy stored within the capacitor 312 is not used to generate the pacing pulses. The capacitor 312 may be electrically connected in parallel with the CG circuit 306 and the switching circuit 310 at the time that the CG circuit 306 generates a pacing pulse and the output 308 receives that pacing pulse. The generation of the pacing pulses by the CG circuit 306 and the receipt of the pacing pulses at the output 308 may be independent of the capacitor 312. For example, the pacing pulses may bypass the capacitor 312 along the conductive pathway from the CG circuit 306 to the switching circuit 310 and the output 308. The pacing pulses are not stored, even temporarily, within the capacitor 312. The capacitor 312 may function like a buffer to reduce ripples or slight fluctuations in the current of the pacing pulses exiting the secondary winding 320 of the transformer 316. By buffering or filtering the pacing pulses, the capacitor 312 may assist, at least slightly, in shaping the pacing pulses to have constant current.

In the low voltage mode, the control circuit 314 controls the CG circuit 306 and the switching circuit 310 according to a second protocol to deliver the pacing pulses. The protocol includes closing the switching circuit 310 to provide an electrically conductive pathway from the CG circuit 306 to the output 308. Then, the control circuit 314 closes the CG circuit 306 to convey power from the battery 272 (shown in FIG. 2) or other power source to the transformer 316. The primary winding 318 of the transformer 316 may be activated by controlling the switch device 322 to generate the pacing pulses, as described herein with reference to FIG. 5. The pacing pulses are inducted across the transformer 316 and received by the secondary winding 320. Because the switching circuit 310 is in the closed, conductive state, the pacing pulses received by the secondary winding 320 are directly conveyed through the switching circuit 310 to the output 308. Stated differently, the pathway between the secondary winding 320 and the output 308 is established prior to the pacing pulse being generated by the CG circuit 306. While each pacing pulse is being generated by the CG circuit 306, the control circuit 314 manages the switching circuit 310 to provide a closed, electrically conductive pathway between the CG circuit 306 and the output 308. The pacing pulses bypass the capacitor 312, without charging the capacitor 312.

The pacing pulse directed to the output 308 is delivered by an electrode of the implantable system 300, such as a non-transvenous lead 304. After delivery of the pacing pulse, the switching circuit 310 and the CG circuit 306 are transitioned to open, non-conductive and/or non-active states. The cycle may repeat for each pulse of the pacing pulses.

The capacitor 312 optionally may have some stored charge during the generation and delivery of the pacing pulses. For example, the charge stored in the capacitor 312 may be residual charge left over after generating one or more shocks during the first phase therapy. During the low voltage mode, some of the stored charge in the capacitor 312 may bleed out of the capacitor 312, and the remainder acts to prime the capacitor 312 in preparation for the next shocking pulse. Optionally, the IMD 302 may include a dump circuit that includes at least one resistive element for discharging excess electrical energy from capacitor 312 as heat after transitioning from the high voltage mode to the low voltage mode.

Figure 5:
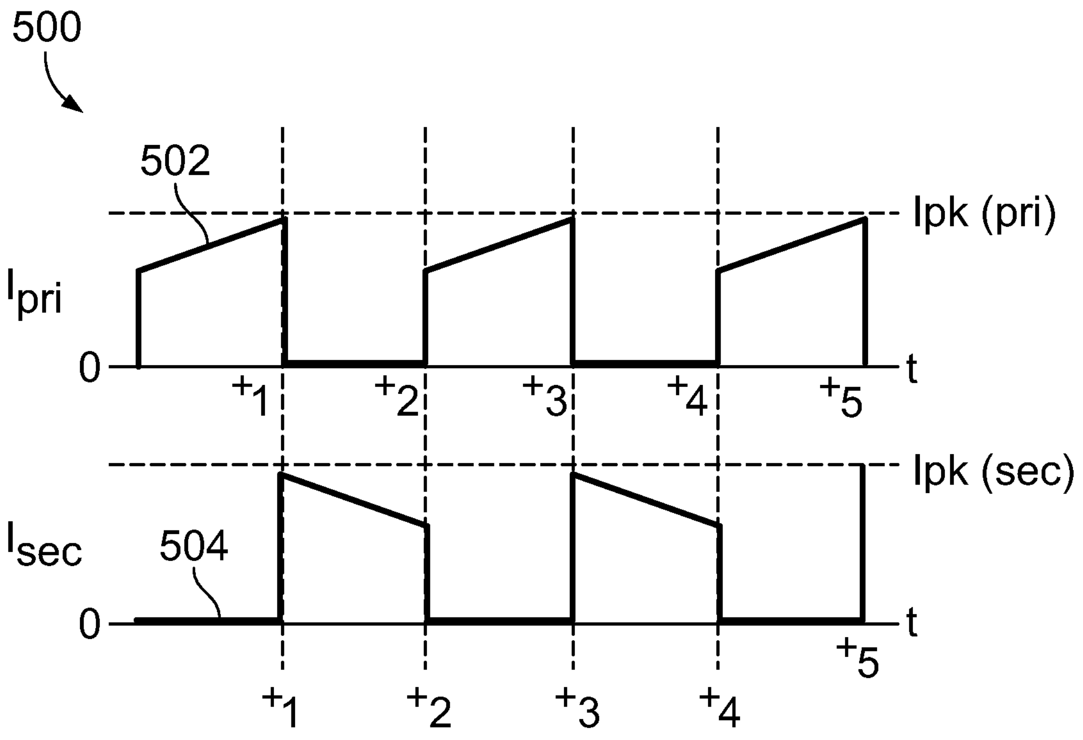
FIG. 5 is a current waveform diagram depicting electrical current activity over time within a transformer of the IMD according to an embodiment.

With continued reference to FIG. 4, FIG. 5 is a current waveform diagram 500 depicting electrical current activity over time within the transformer 316 of the IMD 302 according to an embodiment. The diagram 500 shows a current waveform 502 at the primary winding 318 and a current waveform 504 at the secondary winding 320. The diagram 500 may represent the current at the transformer 316 when controlled by the control circuit 314 during the low voltage mode to provide the pacing pulses.

The transformer 316 may be a flyback transformer that stores energy in the gap of the core. At the start of the cycle, the control circuit 314 may actuate the switch device 322 of the CG circuit 306 to attain the closed, conducting state, which causes current conduction to the primary winding 318. The current through the primary winding 318 induces a magnetic field and stores energy in the core of the transformer 316. The polarity of the windings 318, 320 reverse biases the diode 324 to ensure that energy is not transferred to the secondary winding 320 while the switch device 322 is in the closed state. During this first portion of the cycle until time $t_1$, current in the primary winding 318 increases over time to store energy in the core.

At time $t_1$, the control circuit 314 opens the switch device 322 to break the conductive pathway to the primary winding 318. The magnetic field drops, and the electrical energy that is stored in the core is transferred to the secondary winding 320. As described above, the switching circuit 310 is set to the closed, conducting state prior to or during the generation of each pacing pulse, so once the secondary winding 320 receives the electrical energy, that energy (e.g., pacing pulse) is immediately conveyed through the switching circuit 310 to the output 308 for delivery to the heart or other patient load. The pacing pulse delivery occurs from $t_1$ to time $t_2$. At $t_2$, the cycle repeats. For example, the control circuit 314 again closes the switch device 322 of the CG circuit 306 to conduct electrical energy into the primary winding 318 for temporarily storing energy in the core of the transformer 316 until time $t_3$.

When the switch device 322 is opened at $t_1$, the current in the secondary winding 320 is at the peak level, and the current gradually decreases as the energy stored in the transformer 316 is transferred to the load. The control circuit 314 may close the switch device 322 at $t_2$ before all of the flyback stored energy is transferred to the secondary winding 320, so the current through the secondary winding 320 does not reach zero. For example, the current does not decrease all the way to zero from time $t_1$ to time $t_2$. The control circuit 314 may operate the switch device 322 to cycle between the closed and open states with sufficient frequency to provide continuous conduction across the transformer 316. The control circuit 314 may cycle the switch device 322 of the CG circuit 306 many times to produce each constant current pacing pulse.

Figure 6:
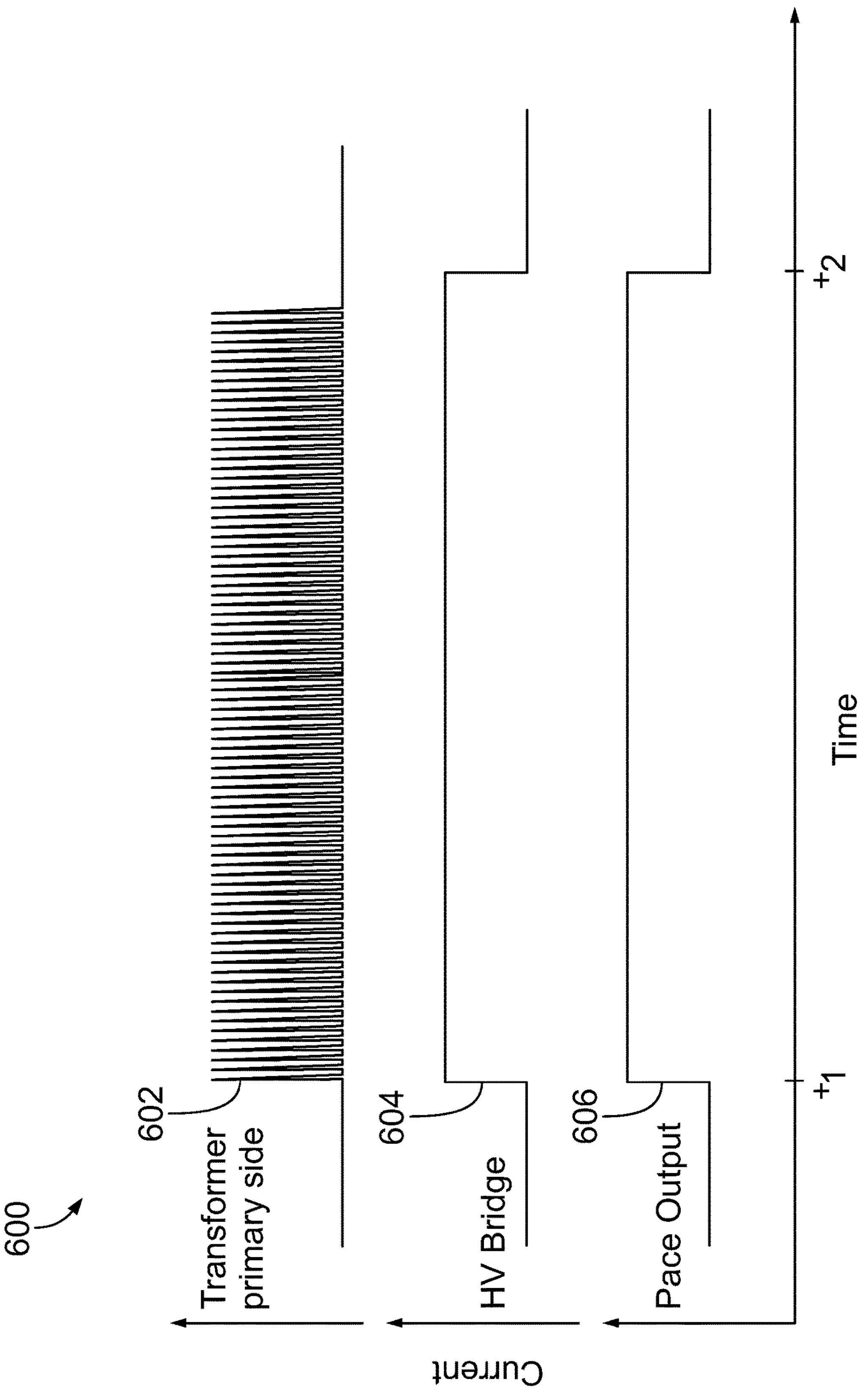
FIG. 6 is a current diagram showing electrical current waveforms over time at different locations in the IMD to deliver a pacing pulse according to an embodiment.

FIG. 6 is a current diagram 600 showing electrical current waveforms over time at different locations in the IMD 302 to deliver a pacing pulse according to an embodiment. The diagram 600 includes a first waveform 602 which depicts the current at the primary winding 318 of the transformer 316. A second waveform 604 depicts the current at the switching circuit 310 (e.g., HV bridge), and a third waveform 606 depicts current at the pace output 308. The first waveform 602 at the primary winding 318 periodically oscillates between times $t_1$ and $t_2$. Optionally, the waveform 602 may represent an extended duration of the waveform 502 shown in FIG. 5. For example, the waveform 602 may depict the current over more cycles of the control circuit 314 closing and opening the switch device 322 than is shown in the waveform 502.

The waveforms 604, 606 show that, although the current oscillates at the primary winding 318, the induced current that is conducted through the switching circuit 310 and the output 308 has a constant value from time $t_1$ to time $t_2$. The current at the output 308 from $t_1$ to $t_2$ defines a single pacing pulse that is delivered via an electrode to the patient load. The amplitude or value of the constant current pacing pulse may be in a range between 50 mA and 500 mA, such as, for example, 100 mA, 200 mA, or 300 mA. The pulse width of the pacing pulse is the duration from $t_i$ to $t_2$. The pulse width optionally may be on the order of milliseconds, such as about 10 ms. The control circuit 314 may control the pulse width of the pacing pulse by ceasing the cycling of the switch device 322 at or slightly before time $t_2$. The control circuit 314 may maintain the switch device 322 in the open, non-conducting state until the next pacing pulse is to be generated.

The control circuit 314 may open and close the switch device 322 of the CG circuit 306 at a predefined frequency and timing according to a duty cycle. The duty cycle may be stored within the memory 260 (shown in FIG. 2). The control circuit 314 may control the characteristics of the constant current pacing pulses, such as a shape and pulse width of the pulses, by varying the duty cycle of the switch device 322, or more generally the duty cycle of the CG circuit 306. The shape of the pacing pulses may be defined by the current amplitude, polarity, and the like. The polarity of the pacing pulses may be positive or negative and mono-phasic or biphasic. In an embodiment, the control circuit 314 can control the polarity of the pacing pulses by configuring the switch devices 328 of the switching circuit 310.

The control circuit 314 may be configured to vary the duty cycle of the control signals 326 supplied to the CG circuit 306 to modify a shape and/or pulse width of the pacing pulses that have the constant current to adjust the therapy delivered to the patient. For example, the control circuit 314 may adjust the characteristics of the pacing pulses to account for variations in the patient load, which can change over time in the same patient and can vary from patient-to-patient.

Figure 7:
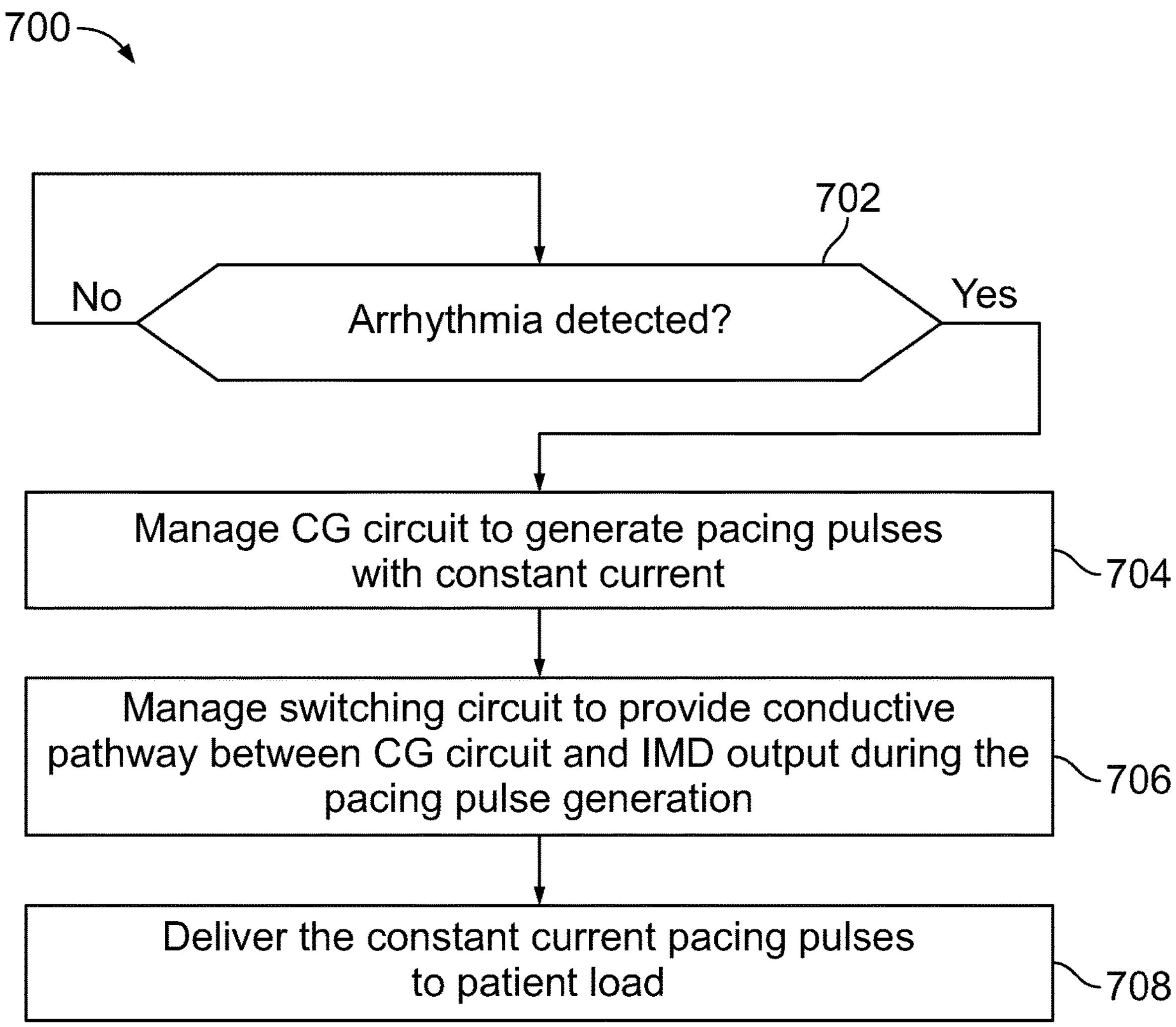
FIG. 7 is a flow chart of a computer-implemented method for delivering stimulation therapy according to an embodiment.

FIG. 7 is a flow chart 700 of a computer-implemented method for delivering stimulation therapy according to an embodiment. The method may be performed by the implantable system 300 shown in FIGS. 3 and 4. The method optionally may include more steps, fewer steps, and/or different steps than shown in FIG. 7. The method starts at 702, at which a determination is made whether an arrhythmia is detected based on signals indicative of heart activity (e.g., CA signals). Processor(s), such as of the control circuit 314, may detect the arrhythmia based on the presence or absence of R-waves in the CA signals. For example, a brady pause arrhythmia may be detected based on an absence of one or more of the R-waves in a segment of CA signals. The control circuit 314 may include an arrhythmia detector module, such as the module 234 of the control circuit 220, that makes the arrhythmia determination at 702. If an arrhythmia is not detected, the flow of the method returns to a sensing operation to monitor for arrhythmias. If an arrhythmia is indeed detected that requires electrical stimulation in the form of pacing pulses, such as ATP, the method proceeds to 704.

At 704, the control circuit 314 manages the CG circuit 306 of the IMD 302 to generate pacing pulses with a constant current at an output 308 of the IMD 302. The output 308 is configured to be connected at least to a non-transvenous lead 304 configured to be implanted outside of a heart (e.g., extra-cardiovascular). The IMD 302 also includes a switching circuit 310 coupled between the CG circuit 306 and the output 308, and one or more capacitors 312 coupled in parallel with the CG circuit 306 and the switching circuit 310.

In an embodiment, the control circuit 314 manages the CG circuit 306 to generate the pacing pulses, for receipt of the pacing pulses at the output 308, independent of the capacitor(s) 312. The control circuit 306 may control the CG circuit 306 to generate (e.g., power) the pacing pulses, without the capacitor(s) 312 generating the pacing pulses. The pacing pulses are generated independent of the capacitor(s) 312 even though the capacitor(s) 312 may be electrically connected in parallel with the CG circuit 306 and the switching circuit 308 during the time that the pacing pulses are generated.

The CG circuit 306 may include a flyback transformer 316, a switch device 322 electrically connected to a primary winding 318 of the flyback transformer 316, and an output diode 324 electrically connected to a secondary winding 320 of the flyback transformer 316. The control circuit 314 may manage the CG circuit 306 by opening and closing the switch device 322 according to a duty cycle to generate the pacing pulses with the constant current at the secondary winding 320.

At 706, the control circuit 314 manages the switching circuit 310 to provide a closed, electrically conductive pathway between the CG circuit 306 and the output 308 during the generation of each of the pacing pulses by the CG circuit 306. For example, the switching circuit 310 primes the delivery mechanism, which is the specific switch devices 328 in the bridge connected to different electrodes, either before or during the generation of each pulse such that once the pacing pulse is received by the secondary winding 320 of the transformer 316, the pacing pulse is conveyed directly through the switching circuit 310 to the output 308, bypassing the capacitor(s) 312.

At 708, the pacing pulses, generated by the CG circuit 306, are delivered to the patient load. At least some of the pacing pulses may be delivered via a non-transvenous lead 304 connected to the output 308 of the IMD 302. The pacing pulses are delivered while the capacitor(s) are electrically connected in parallel with the CG circuit 306 and the switching circuit 310. Optionally, the pacing pulses may be generated and delivered during at least one of post-shock pacing, ATP, or burst fibrillation. For example, the step 702 of detecting an arrhythmia prior to generating the pacing pulses is optional, as the pacing stimulation may also be used independent of an arrhythmic episode or condition. The pacing pulses may be generated during burst fibrillation to induce fibrillation for testing the IMD 302.

Optionally, the method may include varying the duty cycle of the control signals 326 supplied to the CG circuit 306 to define at least one of the shape or pulse width of the pacing pulses that have the constant current.

Optionally, the managing of the CG circuit 306 to generate the pacing pulses with the constant current is a second phase therapy of a multi-phase therapy. Prior to delivering the second phase therapy, the control circuit 314 may deliver a first phase therapy of the multi-phase therapy by managing the one or more capacitors 312 to power one or more shocks to be delivered to the patient load.

The implantable system according to the embodiments disclosed herein is able to selectively provide shock pulses and lower voltage pacing pulses using the same circuit components. The dual-use circuitry enables both defibrillation and constant current pacing/fibrillation therapy while providing component count reduction relative to known implantable systems. In an embodiment, the HV bridge of the switching circuit 310 is controlled to establish the current path before the charge buildup can occur on the high voltage capacitor 312, which enables the pacing pulses to bypass the capacitor 312 even though the capacitor 312 is electrically connected in parallel to the switching circuit 310. With the path established, the current from the CG circuit 306 flows directly through the patient loop at a frequency rate related to the transformer excitation, as opposed to the charge being held in the capacitor 312.

Embodiments of the implantable system include an IMD. The IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

In an embodiment, the IMD may be a subcutaneous IMD that includes one or more structural and/or functional aspects of the device(s) described in U.S. Application Ser. No. 15/973,195, titled "Subcutaneous Implantation Medical Device With Multiple Parasternal-Anterior Electrodes" and filed May 7, 2018; U.S. Application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. The subcutaneous IMD may be an implantable cardioverter-defibrillator (S-ICD) that includes at least one non-transvenous lead.

In an alternative embodiment, the IMD may be a leadless implantable medical device that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the implantable system may include a leadless cardiac monitor (ICM) in addition to the IMD that delivers electrical stimulation therapy. The ICM may include one or more structural and/or functional aspects of the device(s) described in U.S.

Patent Application, U.S. patent application Ser. No. 15/084,373, filed Mar. 29, 2016, entitled, "Method And System To Discriminate Rhythm Patterns In Cardiac Activity."

All references, including publications, patent applications and patents, cited herein are hereby incorporated by reference to the same extent as if each reference were individually and specifically indicated to be incorporated by reference and were set forth in its entirety herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein.

The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof)

may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD), comprising:

a case including an output configured to be connected to a lead;

a current generator (CG) circuit configured to generate pacing pulses at the output, the CG circuit having a transformer with a primary winding and a secondary winding, a switch device connected with the primary winding, and an output diode connected with the secondary winding, the switch device configured to control conduction of electrical energy from a power source to the CG circuit;

a switching circuit coupled in parallel with the CG circuit and the output between the output diode of the CG circuit and the output;

one or more capacitors coupled in parallel with the CG circuit and the switching circuit between the output diode of the CG circuit and the switching circuit; and a control circuit coupled to the CG circuit and the switching circuit, the control circuit configured to manage the CG circuit during a low voltage mode to generate the pacing pulses, the control circuit configured to control the CG circuit and the switching circuit during a high voltage mode to charge the one or more capacitors and use the electrical energy stored in the one or more capacitors to deliver one or more shock pulses to the output, wherein, during the low voltage mode, the control circuit is configured to close the switching circuit to provide a closed, electrically conductive pathway between the secondary winding and the output, and to control the CG circuit such that the pacing pulses are generated from the secondary winding and conducted through the switching circuit to the output without the one or more capacitors or any other capacitor between the CG circuit and the switching circuit generating the pacing pulses.

2. The IMD of claim 1, wherein the control circuit is configured to manage the CG circuit during the low voltage mode to generate the pacing pulses having a constant current at the output.

3. The IMD of claim 1, wherein the control circuit is configured to vary a duty cycle of control signals supplied to the CG circuit to define a shape of the pacing pulses.

4. The IMD of claim 1, wherein the control circuit is configured to vary a duty cycle of control signals supplied to the CG circuit to define a pulse width of the pacing pulses.

5. The IMD of claim 1, wherein the control circuit is configured to open and close the switch device of the CG circuit according to a duty cycle to generate the pacing pulses at the secondary winding.

6. The IMD of claim 1, wherein the switch device is a first switch device, and the switching circuit is arranged in an H-bridge configuration including the first switch device and a second switch device, a third switch device, and a fourth switch device, wherein the first and second switch devices are coupled in parallel on a first side of the output and the third and fourth switch devices are coupled in parallel on an opposite, second side of the output relative to the first and second switch devices.

7. The IMD of claim 1, further comprising the lead, wherein the lead includes an electrode segment for delivering the pacing pulses from the output to a patient during the low voltage mode and delivering the one or more shock pulses from the output to the patient during the high voltage mode, the electrode segment comprising one or more of a ring electrode, a tip electrode, or a coil electrode.

8. The IMD of claim 7, wherein the electrode segment of the lead is configured to be implanted proximate to a xiphoid process of the patient and a lead body of the lead is configured to extend from the electrode segment along an inter-costal area of the patient to the case.

9. The IMD of claim 1, further comprising the lead, wherein the lead includes a first electrode segment and a second electrode segment spaced apart from each other along a length of the lead, wherein the output is configured to convey the one or more shock pulses to at least one of the first electrode segment or the second electrode segment for delivering electrical stimulation therapy to a patient.

10. The IMD of claim 1, wherein the output includes a plurality of terminals electrically connected to different electrodes on at least one of the lead or the case, wherein the control circuit is configured to control the switching circuit to select a subset of the electrodes to define an electrode vector for delivering at least one of the pacing pulses or the one or more shock pulses.

11. The IMD of claim 1, further comprising one or more physiological sensors disposed on or within the case and communicatively connected to the control circuit, the one or more physiological sensors configured to monitor one or more of respiration rate, pH of blood, ventricular gradient, physical activity, body movement, posture, or minute ventilation of a patient in which the case is implanted.

12. The IMD of claim 1, wherein the control circuit is configured to manage the CG circuit to generate the pacing pulses by opening and closing the switch device of the CG circuit according to a duty cycle.

13. The IMD of claim 1, further comprising the power source within the case, the power source configured to supply the electrical energy to the CG circuit to power the CG circuit for generating the pacing pulses.

14. A method comprising:

managing, via a control circuit, a current generator (CG) circuit of an implantable medical device (IMD) to generate pacing pulses at an output of the IMD during a low voltage mode, the pacing pulses configured to be delivered to a patient via a lead implanted within the patient, the CG circuit having a transformer with a primary winding and a secondary winding, a switch device connected with the primary winding, and an output diode connected with the secondary winding, wherein the IMD further comprises a switching circuit and one or more capacitors, the switching circuit coupled in parallel with the CG circuit and the output between the output diode of the CG circuit and the output, the one or more capacitors coupled in parallel with the CG circuit and the switching circuit between the output diode of the CG circuit and the switching circuit;

controlling conduction of electrical energy from a power source to the CG circuit using the switch device;

closing, via the control circuit, the switching circuit to provide a closed, electrically conductive pathway between the secondary winding and the output during the low voltage mode so that the pacing pulses are generated from the secondary winding and conducted through the switching circuit to the output without the one or more capacitors or any other capacitor between the CG circuit and the switching circuit generating the pacing pulses;

switching from the low voltage mode to a high voltage mode; and controlling the CG circuit and the switching circuit, via the control circuit, to charge the one or more capacitors during the high voltage mode and use electrical energy stored in the one or more capacitors to deliver one or more shock pulses to the output.

15. The method of claim 14, wherein managing the CG circuit to generate the pacing pulses during the low voltage mode comprises controlling the CG circuit to generate the pacing pulses independently of the one or more capacitors.

16. The method of claim 14, wherein managing the CG circuit to generate the pacing pulses during the low voltage mode comprises controlling the CG circuit to generate the pacing pulses that have a constant current at the lead.

17. The method of claim 14, further comprising:

monitoring, via one or more physiological sensors, signals indicative of heart activity, wherein the switching from the low voltage mode to the high voltage mode is responsive to detecting, via the control circuit, an arrhythmia based on the signals indicative of heart activity.

* * * * *